United States Patent
Formolo et al.

(10) Patent No.: US 11,237,146 B2
(45) Date of Patent: Feb. 1, 2022

(54) FIELD DEPLOYABLE SYSTEM TO MEASURE CLUMPED ISOTOPES

(71) Applicants: Michael J. Formolo, The Woodlands, TX (US); Michael Lawson, Spring, TX (US); Cara L. Davis, Houston, TX (US)

(72) Inventors: Michael J. Formolo, The Woodlands, TX (US); Michael Lawson, Spring, TX (US); Cara L. Davis, Houston, TX (US)

(73) Assignee: ExxonMobil Upstream Research Company, Spring, TX (US)

(*) Notice: Subject to any disclaimer, the term of this patent is extended or adjusted under 35 U.S.C. 154(b) by 572 days.

(21) Appl. No.: 15/049,833

(22) Filed: Feb. 22, 2016

(65) Prior Publication Data

US 2016/0258922 A1 Sep. 8, 2016

Related U.S. Application Data

(60) Provisional application No. 62/127,151, filed on Mar. 2, 2015.

(51) Int. Cl.
*G01N 33/24* (2006.01)
*E21B 47/11* (2012.01)
*E21B 49/00* (2006.01)

(52) U.S. Cl.
CPC ............ *G01N 33/241* (2013.01); *E21B 47/11* (2020.05); *E21B 49/00* (2013.01)

(58) Field of Classification Search
CPC .............................. G01N 33/241; E21B 49/00
See application file for complete search history.

(56) References Cited

U.S. PATENT DOCUMENTS

| | | |
|---|---|---|
| 5,388,456 A | 2/1995 | Kettel |
| 6,613,520 B2 | 9/2003 | Ashby |
| 7,124,030 B2 | 10/2006 | Ellis |
| 7,174,254 B2 | 2/2007 | Ellis |
| 7,529,626 B1 | 5/2009 | Ellis |
| 8,071,295 B2 | 12/2011 | Ashby |
| 8,316,934 B2 | 11/2012 | Pietrobon |
| 8,476,016 B2 | 7/2013 | Ashby |
| 8,505,375 B2 | 8/2013 | Smalley |
| RE44,728 E | 1/2014 | Pope et al. |

(Continued)

FOREIGN PATENT DOCUMENTS

WO    WO 2013071189 A1 *  5/2013 ......... E21B 47/1015

OTHER PUBLICATIONS

Eller et al., "Clumped-isotope geochemistry—The study of naturally-occuring, multiply-substituted isotopologues". Earth and Planetary Science Letters, 262 (2007) 309-327.*

(Continued)

*Primary Examiner* — Vincent Wall
(74) *Attorney, Agent, or Firm* — ExxonMobil Upstream Research Company—Law Department (57) ABSTRACT

A system and method is provided for enhancing hydrocarbon production. The method and system involve geochemistry analysis and include multiply substituted isotopologue and position specific isotope geochemistry. The method and system involve using clumped isotope and position-specific isotope signatures to enhance reservoir surveillance operations.

12 Claims, 5 Drawing Sheets

(56) References Cited

U.S. PATENT DOCUMENTS

| | | | |
|---|---|---|---|
| 8,760,657 | B2 | 6/2014 | Pope et al. |
| 8,950,251 | B2 | 2/2015 | Valentine |
| 2008/0147326 | A1 | 6/2008 | Ellis |
| 2010/0268469 | A1* | 10/2010 | Harrison ............... G01N 9/002 702/12 |
| 2011/0250582 | A1 | 10/2011 | Gates et al. |
| 2012/0134749 | A1 | 5/2012 | Darrah |
| 2013/0091925 | A1 | 4/2013 | Darrah et al. |
| 2013/0103337 | A1 | 4/2013 | Eiler |
| 2013/0116126 | A1 | 5/2013 | Ashby et al. |
| 2014/0011692 | A1 | 1/2014 | Ashby |
| 2014/0138528 | A1 | 5/2014 | Pope et al. |
| 2014/0162274 | A1 | 6/2014 | Kunin et al. |
| 2014/0250999 | A1* | 9/2014 | Lawson .............. E21B 47/1015 73/152.23 |
| 2015/0022202 | A1* | 1/2015 | Song ....................... G01V 3/14 324/307 |
| 2015/0038348 | A1 | 2/2015 | Ashby et al. |
| 2016/0178786 | A1* | 6/2016 | Badri ...................... G01V 3/32 324/303 |

OTHER PUBLICATIONS

Stopler et al., "Formation temperatures of thermogenic and biogenic methane", Science 2014, vol. 244, No. 6191, pp. 1500-1503.*
Webb et al., "Position-Specific and Clumped Stable Isotope Studies: Comparison of the Urey and Path-Integral Approaches for Carbon Dioxide, Nitrous Oxide, Methane, and Propane", The Journal of Physical Chemistry A, Dec. 2013, pp. 467-474.*
Majid et al., "Potential of NMR Spectroscopy in the Characterization of Nonconventional Oils", Journal of Fuels, vol. 2014, Article ID 390261, 7 pages, http://dx.doi.org/10.1155/2014/390261(Jan. 2, 2014) (Year: 2014).*
Ono et al., "Measurement of a Doubly Substituted Methane Isotopologue, 13CH3D, by tunable infrared laser direction absorption spectroscopy", Anal. Chem., 2014 86, 6487-6494 (Year: 2014).*
Berner, U., et al. (1988), "Maturity Related Mixing Model for Methane, Ethane and Propane, Based on Carbon Isotopes", Advances in Organic Geochemistry, vol. 13, Nos. 1-3, pp. 67-72.
Stahl, W.J., (1977), "Carbon and Nitrogen Isotopes in Hydrocarbon Research and Exploration", Chemical Geology, vol. 20, pp. 121-149.
Chung, H.M., et al., (1979), "Use of Stable Carbon Isotope Compositions of Pyrolytically Derived Methane as Maturity Indices for Carbonaceous Materials", Geochimica et Cosmochimica Acta, vol. 43, pp. 1979-1988.
James, A.T., (1990), "Correlation of Reservoired Gases Using the Carbon Isotopic Compositions of Wet Gas Components", The American Association of Petroleum Geologists Bulletin, vol. 74, No. 9, pp. 1441-1458.
Whiticar, M.J., (1996), "Stable Isotope Geochemistry of Coals, Humic Kerogens and Related Natural Gases", vol. 32, pp. 191-215.
Stolper, D.A., et al. (2014), "Formation Temperatures of Thermogenic and Biogenic Methane", Science, vol. 344, pp. 1500-1503.

Stolper, D.A., et al., (2014), "Combined 13C-D and D-D Clumping in Methane: Methods and Preliminary Results", Geochimica et Cosmochimica Acta, vol. 126, pp. 169-191.
Urey, H.C., et al., (1933), "Some Thermodynamic Properties of the H1H2, H2H2 Molecules and Compounds Containing the H2 Atom", Journal of Chemical Physics, vol. 1, pp. 137-143.
Bigeleisen, J., et al., (1947), "Calculation of Equilbrium Constants for Isotopic Exchange Reactions", The Journal of Chemical Physics, vol. 15, No. 5., pp. 261-267.
Richet, R., et al., (1977), "A Review of Hydrogen, Carbon, Nitrogen, Oxygen, Sulphur, and Chlorine Stable Isotope Fractionation Among Gaseous Molecules", Ann. Rev. Earth Planet. Sci., vol. 5, pp. 65-110.
Vidler, M., et al., (2000), "Accurate Partition Function and Thermodynamic Data for Water", Journal of Chemical Physics, vol. 113, No. 21, pp. 9766-9771.
Liu, Q., et al., (2010), "On the Proper Use of The Bigeleisen-Mayer Equation and Corrections to It in the Calculation of Isotopic Fractionation Equilibrium Constants", Geochimica et Cosmochimica Acta, vol. 74, pp. 6965-6983.
Bloino, J., et al., (2012), "General Perturbative Approach for Spectroscopy, Thermodynamics, and Kinetics: Methodological Background and Benchmark Studies", J. Chem. Theory Comput., vol. 8, pp. 1015-1036.
Truhlar, D.G., et al., (1991), "Simple Perturbation Theory Estimates of Equilibrium Constants From Force Fields", J. Chem. Phys., vol. 94 (1), pp. 357-359.
Webb, M.A., et al., (2014), "Position-Specific and Clumped Stable Isotope Studies: Comparison of the Urey and Path-Integral Approaches for Carbon Dioxide, Nitrous Oxide, Methane, and Propane", J. Phys. Chem. A, vol. 118, pp. 467-474.
Rustad, J.R., et al., (2010), "Calculation of Boron-Isotope Fractionation Between B(OH)3(aq) and B(OH)4-(aq)", Geochimica et Cosmochimica Acta, vol. 74, pp. 2843-2850.
Wang, Y., et al., (2009), "Equilibrium 2H/1H Fractionations in Organic Moldecules: I. Experimental Calibration of Ab Initio Calculations", Geochimica et Cosmochimica Acta, vol. 73, pp. 7060-7075.
Reeves, E.P., et al., (2012), "Hydrogen Isotope Exchange Between n-Alkanes and Water Under Hydrothermal Conditions", Geochimica et Cosmochimica Acta, vol. 77, pp. 582-599.
Glasstone, S., et al., (1941), "The Theory of Rate Processes", McGraw-Hill, New York, pp. 249.
Burnham, A.K., et al., (1989), "A Chemical Kinetic Model of Vitrinite Maturation and Reflectance", Geochimica et Cosmochimica Acta, vol. 53, pp. 2649-2657.
Sweeney, J. J., et al., (1990), "Evaluation of a Simple Model of Vitrinite Reflectance Based on Chemical Kinetics", The American Association of Petroleum Geologists Bulletin, vol. 74, No. 10, pp. 1559-1570.
Magoon, L.B., et al., (1994), "The Petroleum System—From Source to Trap", AAPG Memoir 60, pp. 3-24.
Rustad, J.R., et al., (2007), "Ab Initio Calculation of Isotopic Fractionation in B(OH)3(aq) and BOH4-(aq)", JACS Communications, pp. 2222-2223.
Eiler, J. M. (2007) ""Clumped-isotope" geochemistry—The study of naturally-occurring, multiply-substituted isotopologues". *Earth and Planetary Science Letters*, vol. 262, No. 3-4, pp. 309-327.

* cited by examiner

FIELD DEPLOYABLE SYSTEM TO MEASURE CLUMPED ISOTOPES

CROSS-REFERENCE TO RELATED APPLICATION

This application claims the benefit of U.S. Provisional Application No. 62/127,151 filed Mar. 2, 2015 entitled "FIELD DEPLOYABLE SYSTEM TO MEASURE CLUMPED ISOTOPES", the entirety of which is incorporated by reference herein.

FIELD OF THE INVENTION

The present disclosure relates generally to the field of geochemistry including multiply substituted isotopologue and position specific isotope geochemistry. More particularly, the present disclosure describes a field deployable instrumentation capable of measuring clumped isotope and position-specific isotope signatures of hydrocarbons. The system includes spectroscopic-based isotope analysis and nuclear-magnetic resonance techniques integrated with conventional measurements of composition and compound specific isotopes that can be utilized in field settings to aid in reservoir surveillance and production allocation by measuring clumped isotopes and position specific isotope signatures of hydrocarbon and non-hydrocarbon compounds.

BACKGROUND

This section is intended to introduce various aspects of the art, which may be associated with exemplary embodiments of the present disclosure. This discussion is believed to assist in providing a framework to facilitate a better understanding of particular aspects of the present invention. Accordingly, it should be understood that this section should be read in this light, and not necessarily as admissions of prior art.

Hydrocarbons can be thermogenic or biogenic in origin. Biogenic hydrocarbons are generally restricted to gases and lower molecular weight hydrocarbons generated from the microbial utilization of buried organic matter in the subsurface at temperatures less than 100° C. The generation of these hydrocarbons usually occurs early during sediment burial (e.g., primary biogenic gas), but can also occur during the degradation of thermogenic hydrocarbons (e.g., secondary biogenic gas).

Thermogenic hydrocarbons, such as liquids or gases, are generated in the subsurface from source rocks rich in organic matter. Following initial deposition, source rocks are buried and subjected to increasing temperature and pressure with increasing burial. Thermogenic hydrocarbons are generated when the source rocks reach temperatures sufficient for the thermal conversion of organic material to kerogen and then to free liquid and/or gaseous hydrocarbon phases, which is a process called source rock maturation. Upon generation, the hydrocarbons may either be retained in the source rock (e.g., unconventional resources) or subsequently be expulsed from the source rock and migrate in the subsurface to reservoir rocks, such as sandstones or limestones, that have sufficient porosity, structure and an adequate seal that make them capable of trapping the hydrocarbon phase(s), providing a location for hydrocarbons to accumulate. Alternatively, hydrocarbons may migrate to a surface location, which may be referred to as a seep.

As may be appreciated, any hydrocarbons present in the subsurface may be stored and preserved in a reservoir or they may be subjected to different forms of alteration. For example, biodegradation is the process of degradation or consumption of hydrocarbons by micro-organisms. Similarly, hydrocarbons may be thermally altered by exposure to temperatures above there thermal stability. Alternatively, hydrocarbons may be oxidized or consumed in processes, such as thermochemical sulfate reduction. Non-hydrocarbon compounds, comprising for example $CO_2$, $N_2$, and/or $H_2S$ may also be present in a reservoir gas or fluid. These are contributed from processes, such as maturation, high temperature release from sediments and thermochemical sulfate reduction coupled to the oxidation of organic compounds.

Conventional tools, which include wireline sampling and production logging tests, are costly, time consuming and may be ineffective in certain reservoirs. Monitoring geochemical variations on a production time-scale (e.g., time-lapse geochemistry) may constrain reservoir hydrocarbon signatures while drilling or during production. As such, drilling technology has recently focused on the development of real-time stable isotope measurements (e.g., $\delta^{13}C$) of subsurface fluids to constrain reservoir fluids (e.g., oil and gas) signatures, while drilling. These conventional systems include fluid logging and analysis in real time. These types of conventional systems analyze fluid samples from the well to provide a quantitative analysis of certain hydrocarbon components, such as $C_1$ to $C_5$. Such measurements may provide initial end-member isotope signatures that can be used to evaluate reservoir connectivity or to characterize a baseline for future reservoir surveillance activities.

However, these conventional systems are limited and do not provide sufficient information about the hydrocarbons formation and generation. For example, certain hydrocarbon gases have a limited variety of hydrocarbon compounds for which bulk stable isotopes can be determined (i.e. only methane, ethane, and propane with little or no butane or higher hydrocarbons). Furthermore, processes that impact the non-clumped and/or position specific isotopic signatures of these compounds provide a narrow range in the variability in the signatures that often give rise to similar signatures that result from different histories of generation. That is, the origin of stable isotopic signatures can be non-unique, even for separate reservoir compartments, diminishing their utility for connectivity and surveillance applications.

There remains a need in the industry for apparatus, methods, and systems to identify and enhance hydrocarbon operations. In particular, conventional techniques do not properly distinguish and/or provide accurate quantitative estimates between the amount of hydrocarbon compounds (e.g., gas or liquid) or the sources of these hydrocarbons that are provided for separate reservoir compartments, diminishing their utility for connectivity and surveillance applications.

SUMMARY

According to disclosed aspects and methodologies, a system and method are provided for a deployable system configured to measure clumped isotope and position-specific isotope signatures of hydrocarbons concurrently with other oil field operations. The system may include spectroscopic-based isotope analysis and nuclear-magnetic resonance techniques integrated with measurements of composition and compound specific isotopes that are performed concurrently with operations. The present techniques may be utilized in field settings to enhance reservoir surveillance by measuring clumped isotopes and position specific isotope signatures of hydrocarbon and non-hydrocarbon compounds.

In one or more embodiments, a method for enhancing hydrocarbon production is described. The method includes providing a field deployable system in fluid communication with a subsurface formation, obtaining one or more hydrocarbon samples from the subsurface formation at a first time and analyzing the samples to determine a baseline geochemical signature, obtaining one or more hydrocarbon samples from the subsurface formation at a second time and analyzing the samples to determine a monitored geochemical signature, and comparing the baseline geochemical signature and the monitored geochemical signature. The field deployable system is configured to determine a geochemical signature of a sample based on clumped isotope and/or position specific isotope geochemistry analysis. The field deployable system is used to analyze each of the hydrocarbon samples obtained at the first time from the subsurface formation for a baseline geochemical signature, where the baseline geochemical signature is based on clumped isotope and/or position specific isotope geochemistry analysis. The field deployable system is then used to analyze each of the hydrocarbon samples obtained at the second time for a monitored geochemical signature, where the monitored geochemical signature is based on clumped isotope and/or position specific isotope geochemistry analysis. The method may further comprise adjusting an exploration, development, or production strategy based on the comparison between the monitored geochemical signature and the baseline geochemical signature. Further, the method may include converting each baseline geochemical signature into a baseline temperature and/or baseline composition; and converting the monitored geochemical signatures into a monitored temperature and/or monitored composition; and comparing the monitored temperature with the baseline temperature and/or the monitored composition with the baseline composition.

In one or more embodiments, a system for enhancing hydrocarbon production is described. The system comprises a field deployable system in fluid communication with a subsurface formation, wherein the field deployable system comprises: a processor; an input device in communication with the processor and configured to receive input data associated with a subsurface formation; memory in communication with the processor, the memory having a set of instructions and an output device that outputs the comparison.

In one or more embodiments, the method or system may include various enhancements. For example, the method may involve identifying a source contribution for the monitored geochemical signature based on the baseline geochemical signature. Further, the method may include obtaining the sample from the subsurface location at a later time is based on a specified event, which may include the detection of elevated hydrocarbon presence from a monitoring module. The method may also include monitoring for molecular changes in one or more of methane, ethane, carbon dioxide, nitrogen; monitoring for bulk changes in mixtures of gases in the monitored geochemical signature; monitoring for stable isotope geochemistry changes in one or more of carbon, hydrogen, nitrogen, and sulfur; and/or monitoring using mud gas sampling techniques to provide a quantitative analysis of certain hydrocarbon components. Moreover, the specified event may be a change in oil field operations.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, fewer than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

In the following section, various terms as used herein are defined below. To the extent a term used in a claim is not defined below, it should be given the definition persons in the pertinent art have given that term in the context in which it is used.

As used herein, "a" or "an" entity refers to one or more of that entity. As such, the terms "a" (or "an"), "one or more", and "at least one" can be used interchangeably herein unless a limit is specifically stated.

As used herein, the terms "comprising," "comprises," "comprise," "comprised," "containing," "contains," "contain," "having," "has," "have," "including," "includes," and "include" are open-ended transition terms used to transition from a subject recited before the term to one or more elements recited after the term, where the element or elements listed after the transition term are not necessarily the only elements that make up the subject.

As used herein, the term "exemplary" means exclusively "serving as an example, instance, or illustration." Any embodiment described herein as exemplary is not to be construed as preferred or advantageous over other embodiments.

As used herein, the term "hydrocarbons" are generally defined as molecules formed primarily of carbon and hydrogen atoms, such as oil and natural gas. Hydrocarbons may also include other elements or compounds, such as, but not limited to, halogens, metallic elements, nitrogen, oxygen, sulfur, hydrogen sulfide ($H_2S$), and carbon dioxide ($CO_2$). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof. Hydrocarbons may be located within or adjacent to mineral matrices within the earth, termed reservoirs. Matrices may include, but are not limited to, sedimentary rock, sands, silicilytes, carbonates, diatomites, and other porous media.

As used herein, "hydrocarbon production" refers to any activity associated with extracting hydrocarbons from a well or other opening. Hydrocarbon production normally refers to any activity conducted in or on the well after the well is completed. Accordingly, hydrocarbon production or extraction includes not only primary hydrocarbon extraction but also secondary and tertiary production techniques, such as injection of gas or liquid for increasing drive pressure, mobilizing the hydrocarbon or treating by, for example chemicals or hydraulic fracturing the wellbore to promote increased flow, well servicing, well logging, and other well and wellbore treatments.

As used herein, the term "isotope" refers to one of two or more atoms with the same atomic number but with different numbers of neutrons. Hydrocarbon molecules may contain a variety of isotopes. Hydrocarbon molecules contain both carbon and hydrogen atoms. Carbon can be present in the molecule as one of two stable isotopes: $^{12}C$ which has 6 protons and 6 neutrons (shown herein as C); and, in much lower concentrations, $^{13}C$, which has 6 protons and 7 neutrons. Similarly, hydrogen can be present in a molecule as one of two stable isotopes: H, which contains 1 proton but no neutron; and, in much lower concentrations, Deuterium (D), which has 1 proton and 1 neutron.

As used herein, the term "signatures" refers to the relative abundances, concentrations and/or ratios of various elements, isotopes, positions within a compound and isotopologues of a given species.

As used herein, the term "isotopologue" refers generally to molecules that have the same chemical composition, but have a different isotopic signature. For example, methane contains one atom of carbon and four atoms of hydrogen. Each atom in the methane structure can contain one of the two stable isotopes of that atom, and as such there are ten possible isotopologues of methane.

As used herein, the term "multiply substituted isotopologue" refers generally to an isotopologue that contains at least two rare isotopes in its structure. For example, a multiply substituted methane isotopologue contain one $^{13}C$ atom and one D atom, or at least 2 D atoms in the absence of a $^{13}C$ atom.

As used herein, the term "clumped isotopologue" refers generally to an isotopologue that contains at least two rare isotopes that share a common chemical bond in its structure. For example, a clumped isotopologue of methane contains one $^{13}C$ atom that shares a chemical bond with at least one D atom.

As used herein, the term "position specific isotope signature" refers generally to a compound that has multiple chemically or structurally distinct positions for a rare isotope to reside. For example, a position specific isotope effect in propane could refer to the position of the $^{13}C$ atom, which can be positioned either at the center of the compound or one of the end positions, or the position of the D atom, which can be attached to either a central or end position carbon.

As used herein, the term "stochastic distribution" refers generally to a system where the stable isotopes in a given population of molecules are distributed randomly among all possible isotopologues of a given species. This stochastic distribution is the reference frame from which deviations are measured and is used to provide a baseline to identify anomalies that may be associated with secondary isotope exchange processes.

According to aspects of the disclosed methodologies and techniques, the multiply substituted isotopologue or position specific isotope effects or signatures of single or numerous co-existing isotopologues of hydrocarbons can be integrated with results from other geochemical approaches that incorporate the relative or absolute concentration and isotopic signature of other hydrocarbon and non-hydrocarbon compounds (e.g., nitrogen, hydrogen sulfide, carbon dioxide, carbon monoxide, helium, neon, argon, krypton, xenon) to enhance monitoring of well and stimulation performance. The present techniques are based on the signatures that provide a unique characterization of fluids derived from different reservoir units, and/or different portions of a reservoir, and identify when and how much communication and/or mixing occurs between the fluids. A unique clumped isotope and position-specific signature for a reservoir fluid may be related to different sources, maturity, alteration, reservoir properties, and/or physical association within a reservoir (adsorbed versus pore space).

In one or more embodiments, the present techniques may include combining multiply substituted isotopologue signatures and position specific isotope effects of hydrocarbon compounds (e.g., $CH_4$, $C_2H_6$, $C_3H_8$, liquid hydrocarbons).

The use of multiply substituted isotopologue and position specific isotope geochemistry in a field deployed system may provide concurrent or real-time data for reservoir surveillance. Regardless of how rapidly data is quantified, the time between sampling of the fluids and data analysis of the multiply substituted isotopologue and position specific isotope geochemistry is reduced compared to conventional practices, specifically relative to offsite analysis, and therefore may provide enhancements to operations by providing more unique data about the samples. The clumped isotope and/or position specific isotope signatures can be utilized to recognize different families of hydrocarbons in the subsurface. These families could be separated by the formation temperature, the source of the hydrocarbons, migration histories of the hydrocarbons, the secondary processes such as mixing and biodegradation the hydrocarbons have been subjected to, or any other mechanism that impacts the clumped isotope and/or specific position isotopic signature of the hydrocarbons. The data can provide constraints on the temperature at which particular processes occur in hydrocarbon systems and how the targeted zones are communicating and/or are related. They may also provide specific signatures of hydrocarbon components in mixed systems. These specific isotopologue signatures may be the result of the different histories of the hydrocarbons (e.g., sources and/or maturities) and the results may enhance the capability to quantitatively monitor multiple sources of hydrocarbons, and characteristics, during reservoir surveillance. When combined and integrated with conventional geochemical techniques, such as molecular (i.e., a determination of the types of compounds present, such as methane, ethane, carbon dioxide, nitrogen), bulk (i.e., a determination of the mixture of compounds present, such as the relative amounts of each compound), stable isotope geochemistry (e.g., carbon, hydrogen, nitrogen, sulfur) of hydrocarbon and non-hydrocarbon gases, molecular geochemistry of oils (e.g., saturate and aromatic compounds), physical measurements (e.g., pressure, volume and temperature), and results from formation testing, the results enhance the capability to quantitatively monitor multiple families of hydrocarbons, which may then be used to enhance oil field operations.

Multiply substituted isotopologue geochemistry is based on the variation in the distribution of isotopes within a molecule that gives rise to molecules that are identical in their elemental composition, but that may differ in the isotopic composition of individual atoms within that molecule. These species are called isotopologues. For example, there are three isotopologues of nitrogen (e.g., $^{14}N_2, ^{15}N^{14}N$ and $^{15}N_2$). An isotopologue in which two or more rare isotopes are present in close proximity (i.e., isotopic "clumps") is called a multiply-substituted isotopologue or clumped isotope (e.g., $^{15}N_2$). The hydrocarbon isotopologues involve hydrocarbon compounds (e.g., those that contain carbon and hydrogen atoms) that have natural isotopes of $^{12}C$, $^{13}C$, $^1H$, or H (deuterium or D). $^{12}C$ represents about 98.93 mole percent (mol. %) of the total carbon on Earth, while $^{13}C$ forms the remaining 1.07 mol. %. Similarly, the isotopic abundance of $^1H$ on earth is 99.985 mol. % while D has an abundance of 0.015 mol. %. Common volatile hydrocarbons have large numbers of isotopologues even considering only the stable isotopes (e.g., methane has 10; ethane has 36; propane has 216). Common isotopologues of methane for example include $^{13}C^1H_3D$ or $^{12}C^1H_4$. In addition to the number of rare isotopes, the distribution of isotopes in the molecule can also provide information. For example, in a linear hydrocarbon compound with three carbon atoms, the rare isotope can take either a central or terminal (end of the molecule) position. Similarly, rare isotopes of hydrogen can occupy different positions. As the size of the hydrocarbon compound increases, the number of positions that these rare isotopes can be situated increases. This effect is called the position specific isotope effect, or isotopomer geochemistry.

The multiply substituted isotopologue and the position specific isotope signature of any molecule are a function of (i) temperature-independent randomly populated processes (stochastic distribution) and (ii) other non-random mass fractionating processes. The stochastic distribution of any set of isotopologues can be determined from the bulk isotope signatures of the species from which it derives. For example, determining the stochastic distribution of isotopologues for methane involves knowledge of the $^{13}C$ and D signatures of methane. At equilibrium, a non-stochastic distribution may result from thermodynamic differences between the different isotopologues. Under non-equilibrium conditions, the non-random processes may be temperature-time dependent isotopic exchange reactions in some hydrocarbons. For example, multiply substituted isotopologue signatures in methane appear to provide equilibrium gas generation temperatures. See, e.g., Stolper et al., Formation temperatures of thermogenic and biogenic methane, Science, 344, p. 1500-1503 (2014). Additional equilibrium or non-equilibrium kinetic isotope exchange processes may also influence the signatures in some hydrocarbon species. These processes may include, but are not limited to, biodegradation, secondary thermal cracking of hydrocarbons, thermochemical oxidation or reduction reactions, mixing or diffusion, physical processes, such as sorption or desorption or transport processes, such as diffusion and advection. These processes may differ in their relative magnitude of the impact on the multiply substituted isotopologue and/or position specific isotope signatures. The combination of all these mechanisms may determine specific clumped isotope and/or positions specific isotope signatures in hydrocarbons that can be utilized to recognize families of hydrocarbons. These processes may also result in changes in the concentrations and isotopic signatures of non-hydrocarbon compounds. By measuring the clumped and position specific isotope signatures of multiple hydrocarbon compounds that may be sensitive to different parameters one can determine the key processes controlling these signatures and quantify the extent of this effect on the sample.

The present techniques involve measuring multiply substituted isotopologue and position specific isotope geochemistry of samples. More particularly, the present techniques involve a field deployable system or instrumentation configured to measure clumped isotope and position-specific isotope signatures of hydrocarbons. The present techniques may include spectroscopic-based isotope analysis and nuclear-magnetic resonance techniques, which may be integrated with conventional measurements of composition and compound specific isotopes, to enhance in reservoir surveillance by measuring clumped isotopes and position specific isotope signatures of hydrocarbon and non-hydrocarbon compounds. The present techniques utilize the clumped isotopes and position specific isotope signatures to provide a unique characterization of hydrocarbon and non-hydrocarbon compounds that derive from different reservoir units, and/or different portions and compartments of a reservoir to understand the origin and history of the compounds, including potential sources and alteration of the hydrocarbons, connectivity and/or compartmentalization of reservoirs during near real-time reservoir surveillance. A unique clumped isotope and position-specific signature for individual compounds may be related to different sources, maturity, alteration, present day or historic reservoir properties, and/or physical association within a reservoir (adsorbed versus pore space). Reservoir surveillance using clumped isotopes and/or position specific isotope techniques may provide more quantitative constraints on the origin, migration and storage history of compounds to improve exploration, development and production efficiency.

With clumped isotopes, multiple isotopologues exist for any given compound, including hydrocarbon compounds, such as methane through higher molecular weight liquid hydrocarbons. These signatures can be sensitive and unique to specific physical variations (e.g., generation and/or reservoir temperature) or alteration processes (e.g., biodegradation) that vary between reservoirs. Thus, the multiple isotopologues provide a mechanism to distinguish between different reservoirs. Accordingly, a field based clumped and position specific isotope system may provide an opportunity to observe and interpret real-time or concurrent data to evaluate reservoir connectivity, allocate production, and recognize contamination from drilling processes, as well as potentially determine the origin and alteration of hydrocarbons. For example, measurements may be performed at a field location and concurrent with drilling operations. The system may be in fluid communication with the drilling equipment or attached to pipelines flowing produced fluids (e.g., hydrocarbons and other compounds obtained in the oil field operations). In addition, the measurements with the present techniques may be a more cost effective and provide more time-sensitive information as compared to conventional sampling and analytical procedures.

For the field deployable system, the measurements of clumped isotopes and/or position specific isotope signature may provide enhancements to the understanding of the generation of hydrocarbons, such as liquids or gases, from the previously mentioned biogenic and thermogenic processes. Each of these processes, including generation, storage and alteration, influences the clumped isotope and/or position specific isotope signature of hydrocarbon compounds that record a history of where they originated, how long they have been stored and what processes they have experienced. Various aspects of the present techniques are described further in FIGS. 1 to 6.

Figure 1:
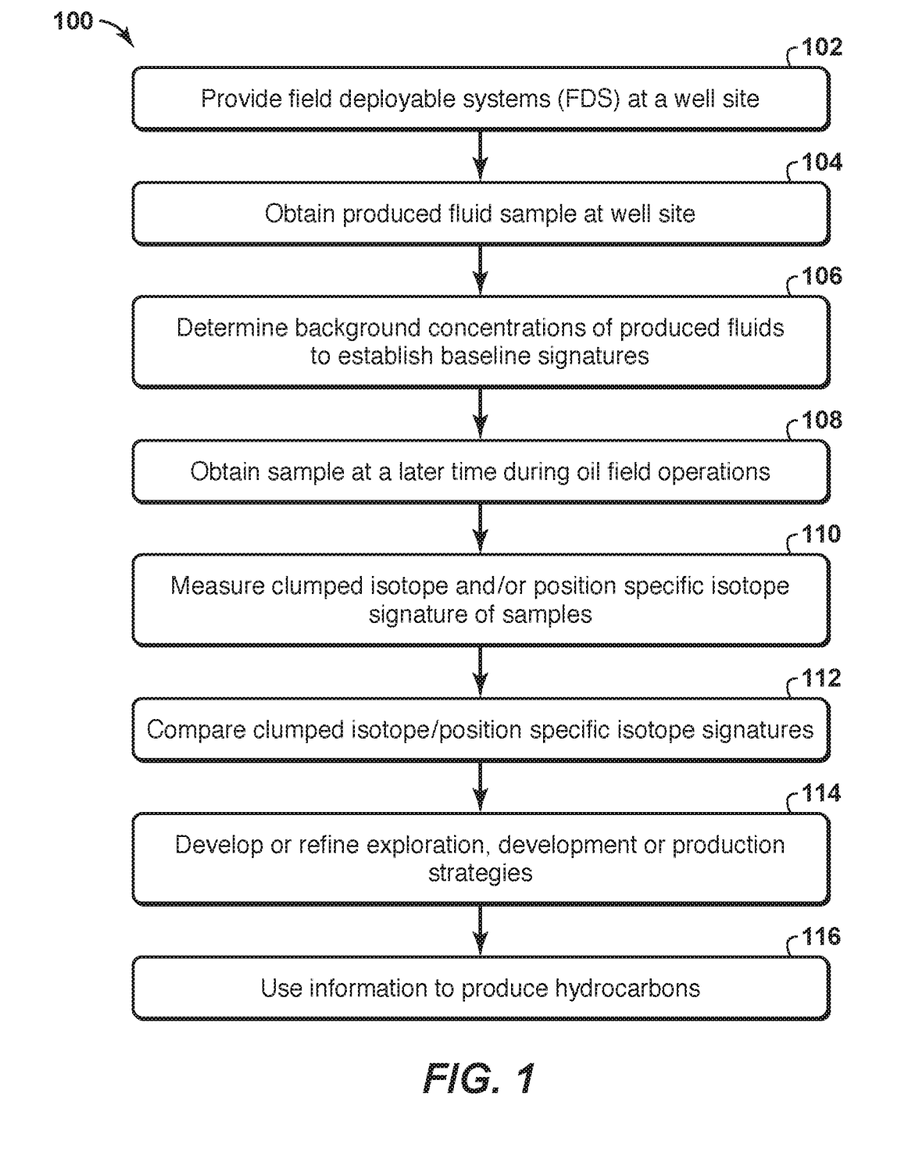
FIG. 1 is a flow diagram of an exemplary method to determine clumped isotope signature and/or position specific isotope signature of produced fluids from a field in accordance with an exemplary embodiment of the present techniques.

FIG. 1 is a flow diagram 100 of an exemplary method to determine clumped isotope or position specific isotope signature of produced fluids from a field in accordance with an exemplary embodiment of the present techniques. For example, this method may be used as a field deployable system that is part of a reservoir surveillance program. The analysis based on such monitoring may be used to adjust or modify exploration, development or production activities, such as hydrocarbon production operations. The field deployable system may utilize spectroscopic, mass spectrometric and/or nuclear magnetic resonance (NMR) instrumentation for reservoir surveillance at field sites. The measurements may be performed in off-line analysis on samples identified for this more diagnostic analysis and/or in concurrent analysis, which may be near continuous to provide for monitoring of fluid clumped and/or position specific isotope signatures while exploration, development or production activities are being performed (e.g., concurrently performed).

In this diagram 100, the field deployable system (FDS) may be provided at a well site, as shown in block 102. The FDS may include a spectroscopic module, mass spectrometric module and/or nuclear magnetic resonance (NMR) module. The FDS may be in fluid communication with the produced fluids. The produced fluids may include hydrocarbons and other non-hydrocarbon fluids produced from a subsurface formation. The produced fluids may be subjected to various filtering and separation operations. Providing the field deployable system at the well site may include disposing the FDS adjacent to other equipment at the well site, which may be installed in fluid communication with mud-gas systems and/or configured to attach to a well head. Monitoring of hydrocarbon responses in the hydrocarbon (e.g., gas or liquids) logging system provides for the establishment of background conditions and conditions that exceed backgrounds, for example elevated hydrocarbon responses when encountering a reservoir. Samples from the background and any other identified region of interest can be directed to the FDS system. The hydrocarbons can be directed to the FDS as a bypass stream or as an in-line stream. Analysis can proceed following any necessary filtering and separation techniques.

At block 104, one or more samples are obtained at a first time. At block 108, one or more samples are obtained at a second time. The samples may include hydrocarbons and/or non-hydrocarbons in in liquid or gas form. The sample may be obtained for each interval within the wellbore, at different time periods, in response to a monitored event, at different intervals or other suitable ranges to provide samples for different regions of the wellbore. For example, the samples may be obtained from different wellbore intervals from 1 meter to 10 meters, from 10 meters to 100 meters, from 100 meters to 500 meters, or from 500 meters to 1000 meters. Alternatively, the samples may be obtained from different identified regions based on seismic interpretations or modeling of the subsurface. Further still, the samples may be obtained at specific time intervals, such as a sample may be obtained once an hour, or from 1 hour to 3 hours, 3 hours to 10 hours, 10 hours to 24 hours, or once a day, or once a week, or other suitable periods of time. Thus, in some embodiments a first sample or series of samples may be taken at a first time, then a second sample or series of samples may be taken at a second time, where the second time is later than the first time. In some embodiments, the second time may be one hour after the first time, or from 1 to 3 hours after the first time, or from 3 to 10 hours after the first time, or from 5 to 10 hours after the first time, or from 10 to 24 hours after the first time, or at least a week after the first time. As an example, the sample may be obtained during drilling operations on samples of mud gas that are known to be from non-reservoir zones or units and from zones that are from reservoirs that are penetrated during drilling.

Then, at block 106, the background concentrations are determined for the produced fluids. This analysis in block 106 may establish a baseline geochemical signature for any background concentration of hydrocarbons in non-reservoir units or zones. The background signatures may include the multiply substituted isotopologue signature and/or position specific isotope signature for the respective sample.

At block 108, a sample is obtained at a second time or later time during oil field operations. The later sample may be referred to as a monitored sample. The later time may be based on an event or specified time period. The sample may be obtained at different time periods and/or in response to a monitored event. For example, the samples may be obtained at specific time intervals, such as a sample may be obtained from 1 hour to 3 hours, 5 hours to 24 hours, 24 hours to 72 hours or weekly. Alternatively, the samples may be obtained to establish a baseline, when zones of increased hydrocarbon presence are identified, and/or when elevated signatures of a compound are identified in other monitoring modules. For example, conventional mud gas sampling techniques, such as analysis of fluid samples (e.g., produced fluids) from the wellbore during drilling or post-drilling monitoring to provide a quantitative analysis of certain hydrocarbon components, such as $C_1$ to $C_5$, may be used to obtain end-member isotope signatures. If this monitoring indicates that an anomaly has occurred, or any sample identified for analysis, the samples can be monitored using the FDS. Also, events related to the operations may trigger the need to analyze hydrocarbon samples using the FDS. An event may be a change in oil field operations, such as restarting from a shut-in or other change in drilling activities, for example.

Regardless, the clumped isotope and/or position specific isotope signature of the sample may be determined, as shown in block 110. The clumped isotope and/or position specific isotope signature may be referred to as a monitored geochemical signature. Then, the determined clumped isotope/position specific isotope signature is compared with other signatures, as shown in block 112. The comparison may involve comparing the monitored geochemical signature from the later obtained sample with the baseline geochemical signatures (e.g., comparing the clumped isotope and/or position specific isotope signatures of the samples). The clumped isotope signature and/or position specific isotope signature of the sample (e.g., liquid and/or gas) is then utilized to differentiate the potential families (e.g., hydrocarbon families). For example, if methane, the primary chemical component of natural gases, is used as an example, it is possible to investigate the potential of forming the clumped doubly substituted isotopologue $^{13}CH_3D$, and the doubly substituted isotopologue $^{12}CH_2D_2$. Methane from different sources (e.g., multiple thermogenic and/or biogenic sources) should have different clumped isotope signatures. Clumped isotope signature and/or position specific isotope signature provide a mechanism to separate the sources of the gases in mixed systems. Also, the comparing the monitored geochemical signature with the baseline geochemical signature may involve comparing the monitored temperature with the baseline temperature or comparing the monitored composition with the baseline composition.

Then, at block 114, the exploration, development or production strategies may be refined or modified. For example, the results of the comparison may be used to support decisions regarding hydrocarbon sources, maturation, and/or other suitable information about the subsurface formation. As another example, if this technology is used during drilling and identifies hydrocarbons that have a signature indicative of a mixture of hydrocarbons generated from two different source rocks, this could suggest a potential for singly sourced hydrocarbon accumulation occurrence up or down dip of the present location. This information could then be used to further explore for hydrocarbons regionally.

In block 116, the strategies may be used to produce hydrocarbons. That is, based on the comparison, drilling of a well may be performed to provide access to the hydrocarbon accumulation. Further, the production may include installing or modifying a production facility for the production of hydrocarbons from the production intervals that provide access to the hydrocarbons in the subsurface formation. The production facility may include one or more units to process and manage the flow of production fluids, such as hydrocarbons and/or water, from the formation. To access the production intervals, the production facility may be coupled to a tree and various control valves via a control umbilical, production tubing for passing fluids from the tree to the production facility, control tubing for hydraulic or electrical devices, and a control cable for communicating with other devices within the wellbore. The strategy may adjust the well locations, fracture depths and patterns, etc.

Further, as another example, it is useful for reserves estimation and well performance prediction to understand the physical origin of hydrocarbons. Both matrix and fracture fluids can contribute to production, as can be sorbed and/or free fluids. Production strategies can differ significantly for these different fluids and it is therefore useful to be able to recognize and monitor the contributions of each. Clumped isotope and position-specific isotope signatures can be affected by sorption and may therefore reflect contribution of adsorbed versus free gas. Signatures for hydrocarbons produced predominantly from fractures may reflect more mixing than fluids produced predominantly from matrix hydrocarbons.

The analysis of the hydrocarbon sample may involve determining the multiply substituted isotopologue signature and/or isotope position specific signature. The measurement of the absolute abundance of isotopologues or position of interest for any given hydrocarbon involves the knowledge of the molecular mass or absorption spectra at which they are present, and hence involves knowledge of the actual identity of each possible isotopologue for that species. Measurement of the abundance of each isotopologue or fragment can be conducted using multiple techniques, such as mass spectrometry, spectroscopy or nuclear magnetic resonance.

As an example, one of the characteristics that impact the isotopologue signature of the hydrocarbons is the temperature of formation or storage. In particular, this temperature can be used to differentiate between different sources and reservoirs of hydrocarbons. This is done through first the conversion of the multiply substituted isotopologue signature and/or position specific isotope signature to temperature. Temperature is an equilibrium signature that can be predicted by molecular modeling of equilibrium concentrations of multiply substituted isotopologue or positional effects, or may be determined empirically by measurements of signatures of a given hydrocarbon compound at different temperatures either in the presence or absence of a catalyst to accelerate equilibrium. Different hydrocarbon species have different rates of equilibration of their multiply substituted isotopologue and position specific effects. For example, the $^{13}CH_3D$ isotopologue in methane may record methane generation temperature. See, e.g., Stolper et al., Science (2014) and preserves the signature even when exposed to different temperatures during migration or uplift of the sediments in which the methane is contained.

The decreasing time interval between sample acquisition, measurement and analysis has numerous valuable reservoir surveillance applications. For example, daily logs of isotope signatures collected during drilling could be utilized to provide information on reservoir and hydrocarbon properties that ultimately are used to inform drilling or production operations. An example of this could be that this information identifies hydrocarbons in one compartment or section of a reservoir that are of a lower quality (e.g., as a result of thermal or biological alteration) than hydrocarbons in a different compartment or section of a reservoir. The operation may be adjusted to return to drilling in the reservoir or compartment with higher quality hydrocarbons in real-time or concurrently with the operations to ensure production of the higher quality produced fluids. Another example may include monitoring of real-time or concurrent clumped or position specific isotope data from analysis of co-mingled hydrocarbons in a production stream to identify changes in the hydrocarbon signature that is associated with an increase in production from one interval or reservoir that had previously been characterized during drilling. This information could suggest the pressure is being drawn down in one reservoir and has resulted in a decreased contribution. This information could then be used to change the production strategy (e.g. decrease the flow from one reservoir or increase flow from other reservoirs) to ensure long term fluid production and maximize the lifespan of the well. These measurements therefore provide a more cost effective and rapid methodology, and allow for early identification of changes that may be missed using current monitoring methodologies and sampling procedures for offsite analytical efforts.

Figure 2:
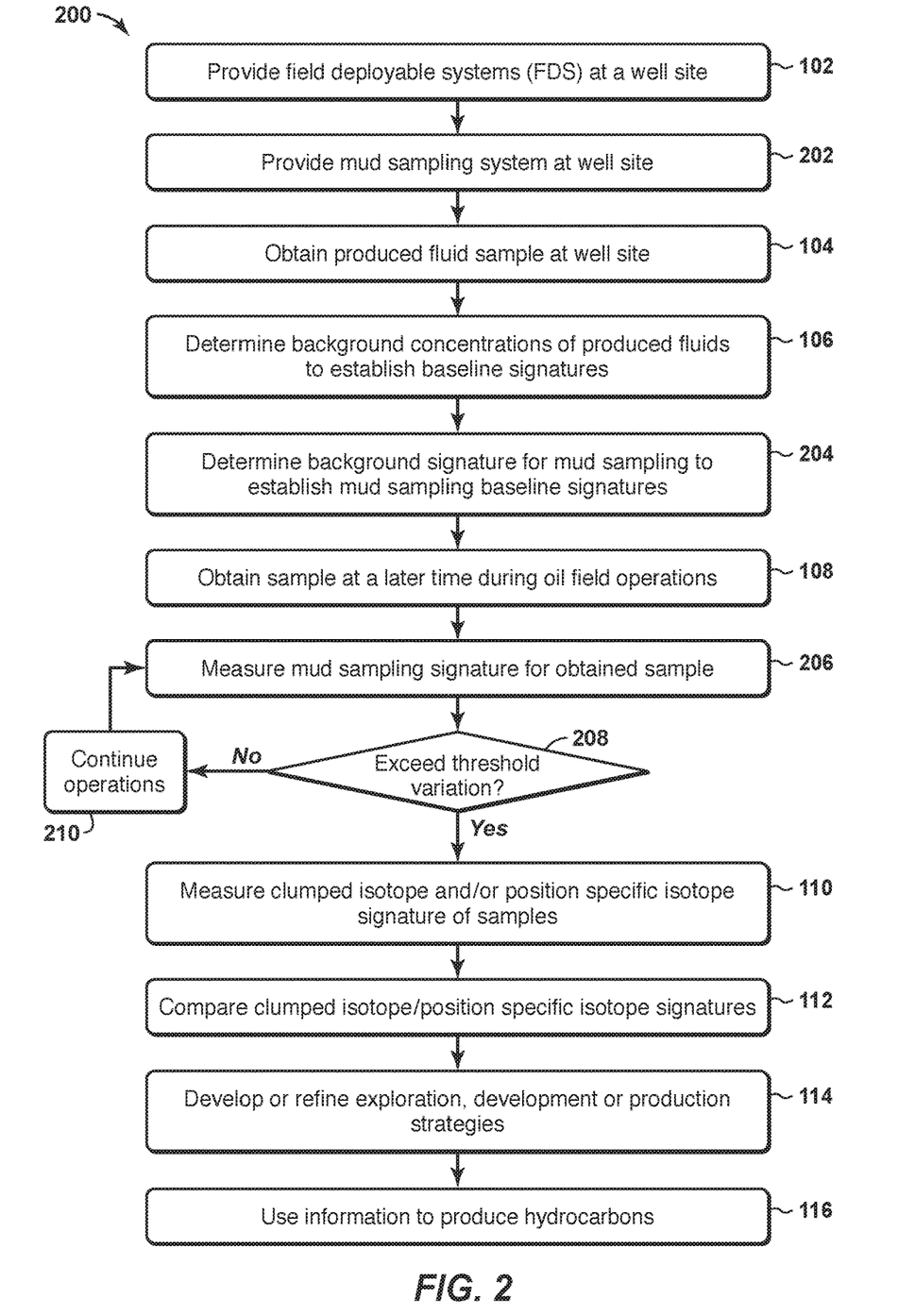
FIG. 2 is a flow diagram of an exemplary method to integrate clumped isotope signature and/or position specific isotope signature of produced fluids with mud sampling techniques from a field in accordance with an exemplary embodiment of the present techniques.

FIG. 2 is a flow diagram 200 of an exemplary method to integrate clumped isotope signature and/or position specific isotope signature of produced fluids with mud sampling techniques from a field in accordance with an exemplary embodiment of the present techniques. In this diagram 200, various blocks, which are labeled with the same reference characters from FIG. 1, are utilized in a manner similar to the description of FIG. 1. However, in this diagram 200, the mud sampling technique is utilized as a measure to determine when the clumped isotope signature and/or position specific isotope signature of produced fluids should be compared to the baseline geochemical signature. Additional monitoring techniques may be utilized to select samples, these could include any logging techniques of hydrocarbons from the wellbore during or post-drilling, or any additional sampling techniques such as wireline or isotube sampling.

In this diagram 100, the field deployable system (FDS) may be provided at a well site, as shown in block 102. In addition, a mud sampling system or a produced gas sampling system is provided at a well site, as shown in block 202. The mud sampling system may be a mud gas sampling techniques known to those skilled in the art. Alternatively, a produced gas sampling system may use produced gas sampling techniques known to those skilled in the art. This technique is a screening method for relative hydrocarbon abundances as part of a continuous logging method. It is common practice and is the monitoring step, or a similar logging method can be used, to visualize background conditions and changes above or below those so that samples can be identified. The mud sampling technique may include analysis of drilling fluid and/or hydrocarbon (e.g., gas or liquid) samples obtained from the wellbore to provide a quantitative analysis of certain hydrocarbon components, such as $C_1$ to $C_5$, and may be used to obtain end-member isotope signatures.

Then, at block 104, a baseline sample is obtained. At block 106, the background concentrations are determined for the produced fluids. Then, at block 204, a background signature for mud sampling (e.g., hydrocarbons) may be determined to establish mud sampling (e.g., hydrocarbon) baseline signatures. The mud sampling baseline signature for any background concentration of hydrocarbons in non-reservoir units or zones. The background signatures may include a specific signature for the respective sample, which is based on the mud sampling technique.

At block 108, a sample is obtained at a later time during oil field operations. Then, at block 206, the mud sampling signature for obtained sample is measured. Then at block 208, the measured mud sampling signature is utilized to determine if a threshold variation is present. The threshold variation may involve comparing the mud sampling signature with the mud sampling baseline signature. Then, if the signatures are below the threshold variation, then the operations continue, as shown in block 210.

However, if the signatures are different above a threshold value, the clumped isotope and/or position specific isotope signature of the sample may be determined, as shown in block 110. Then, the determined clumped isotope/position specific isotope signature is compared with other signatures, as shown in block 112. Further, at block 114, the exploration, development or production strategies may be refined or modified. Finally, in block 116, the strategies may be used to produce hydrocarbons.

Beneficially, this method integrates the mud sampling or produced gas sampling or other available continuous logging monitoring and screening techniques with the clumped isotope and/or position specific isotope signature to further enhance the process. In this manner, the clumped isotope and/or position specific isotope signature is to determine when a variation is detected from the mud sampling or produced gas sampling.

Figure 3:
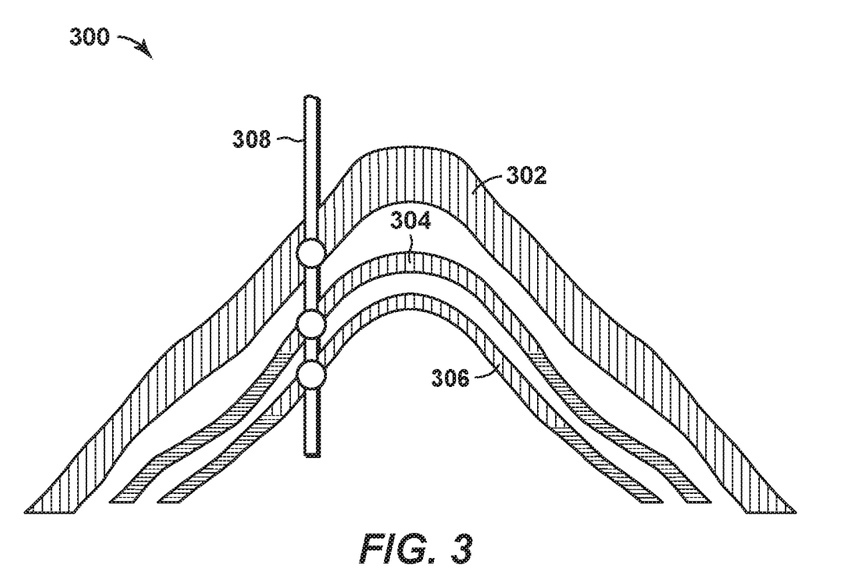
FIG. 3 is a diagram of an exemplary subsurface region.

As an example of the type of formations that may be encounter, FIG. 3 is a diagram 300 of an exemplary subsurface region. In this diagram 300, the clumped and/or position specific isotope signatures may be used in reservoir surveillance to identify the different reservoirs. For example, this diagram 300 has a reservoir A 302, a reservoir B 304 and a reservoir C 306, which are each traversed by a well 308.

As may be appreciated, each of the reservoirs 302, 304 and 306 may have associated clumped isotope signatures. Each reservoir, or hydrocarbon gas, may have individual clumped isotope signature that can be used to differentiate hydrocarbon gases. If signatures are similar among a series of reservoirs then the origin and history of the gases can also be determined. These signatures can be used for reservoir connectivity or reservoir surveillance. For example, the reservoir A 302 has a clumped/position specific isotope signature of A; reservoir B 304 has a clumped/position specific isotope signature of B and reservoir C 306 has a clumped/position specific isotope signature of C.

As an example of different scenarios, the clumped isotope and position specific isotope signatures A, B and C may be unique for the reservoirs 302, 304 and 306, respectfully. Specifically, the clumped isotope and position specific isotope signatures A, B and C are not equal (e.g., $A \neq B \neq C$). These different signatures may arise from differences in the generation, migration and storage history of the hydrocarbons in these different reservoirs. The differences in these signatures may be utilized to calculate the proportion of the total co-mingled fluid production originates from the different reservoirs (e.g., 20% from A of reservoir 302, 50% from B of reservoir 304 and 30% from C of reservoir 306). This information can also be used to confirm that these different reservoirs are not in geochemical communication. This could, for example, involve individual pressure depletion strategies be developed for each reservoir rather than one strategy to deplete the reservoir system in the event that they were in communication.

As a second example scenario, the clumped isotope and position specific signatures A, B and C of hydrocarbon and non-hydrocarbon gases are identical in each reservoir 302, 304 and 306 (e.g., $A=B=C$). This suggests that the hydrocarbons likely have similar histories (e.g., sources, alteration etc.). This information could suggest that the reservoirs are in pressure communication, which may give rise to a different depletion strategy than that developed in the first scenario. This also makes production allocation challenging or not possible to perform because it relies upon different reservoirs 302, 304 and 306 having unique signatures A, B, and C.

As a third example scenario, the clumped isotope and position specific signatures A, B and C of hydrocarbon and non-hydrocarbon gases may be a random distribution of similar and dissimilar values. This distribution may indicate that variable histories are present for the reservoirs 302, 304 and 306 (e.g., sources, alteration, etc.). This variable history is dependent upon the respective signatures.

As shown by the scenarios, the quantification of clumped isotopes and/or position specific isotope signatures of hydrocarbons can be used as part of a reservoir surveillance program. The scenarios include unique isotope signatures, similar isotope signatures, or a combination of similar and dissimilar values among the measured hydrocarbons. These exemplary scenarios rely upon the uniqueness of the clumped isotope and/or position specific isotope signatures relative to the specific hydrocarbons. Thus, the varying scenarios each provide diagnostic information regarding the history of the hydrocarbons and therefore provide information regarding source, alteration, etc.

Figure 4:
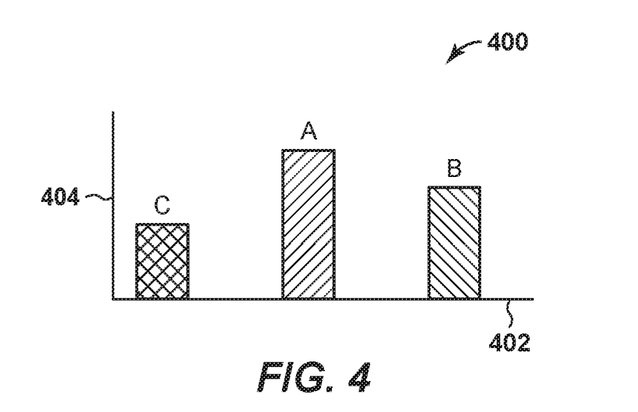
FIG. 4 is a chart of an exemplary distribution of the clumped isotope and/or position specific isotope signatures for the reservoirs of FIG. 3.

FIG. 4 is a chart 400 of an exemplary distribution of the signatures for the reservoirs of FIG. 3. In this chart 400, the signatures A, B and C, which are described above with regard to FIG. 3 represent the reservoirs 302, 304 and 306, are shown along the axis 402 and the isotopic signature is shown along the axis 404. Because the clumped isotopes and/or position specific isotope signatures are unique, these signatures can be utilized for reservoir surveillance activities; for reservoir connectivity analysis; for production allocation; for contamination analysis from drilling processes; for determining the origin of hydrocarbons and for determining the alteration of hydrocarbons in a subsurface formation that includes various reservoirs.

Figure 5:
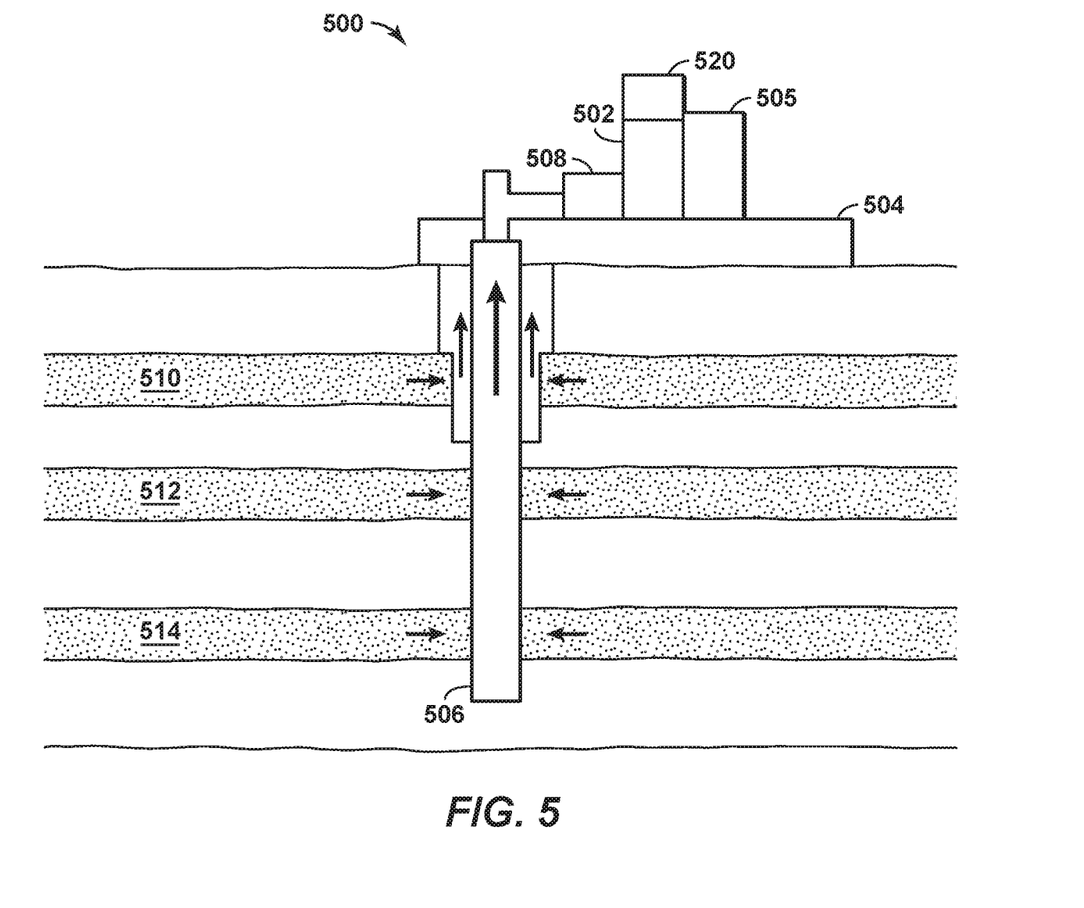
FIG. 5 is a diagram of an exemplary system including a field deployable system at a well site in accordance with an exemplary embodiment of the present techniques.

As an example of how the system may be configured, FIG. 5 is a diagram 500 of an exemplary system including a field deployable system 502 at a well site in accordance with an exemplary embodiment of the present techniques. The system may also include a drill rig 504 and/or a mud sampling system 505 along with other equipment. The well 506 may penetrate reservoirs, such as reservoirs 510, 512 and 514.

The field deployable system 502 may be a clumped isotope and/or position specific isotope system in fluid communication with produced fluids from a well 506. The field deployable system may include an inline sampling module 508 and a controls module 520. The FDS 502 may be in fluid communication with the produced fluids, so that hydrocarbon samples (e.g., liquid and/or gas) can be directed toward the inline sampling module (e.g., a collection device), if needed, for sample preparation and analysis. The controls module 520 may include a computer configured to manage the different measurement modules (e.g., a spectroscopic module, mass spectrometric module and/or nuclear magnetic resonance (NMR) module); to process the samples; and to store signatures.

As shown in this diagram 500, the field deployable system 502 may be installed at the well site downstream of bore hole or well 506. This may also be downstream of mud-gas lines or other logging tools for monitoring and screening so that hydrocarbons may be isolated for preparation and analysis of clumped isotopes and/or position specific isotopes. Various targeted intervals may contribute hydrocarbons, but by targeting hydrocarbons from certain intervals the individual isotope signatures, which are specific to the history of the hydrocarbons, can be determined. These data are then processed as part of the reservoir surveillance program. Data can be utilized for production allocation, to recognize contamination from drilling processes, evaluate the origin of hydrocarbons and identify alteration of the hydrocarbons.

Figure 6:
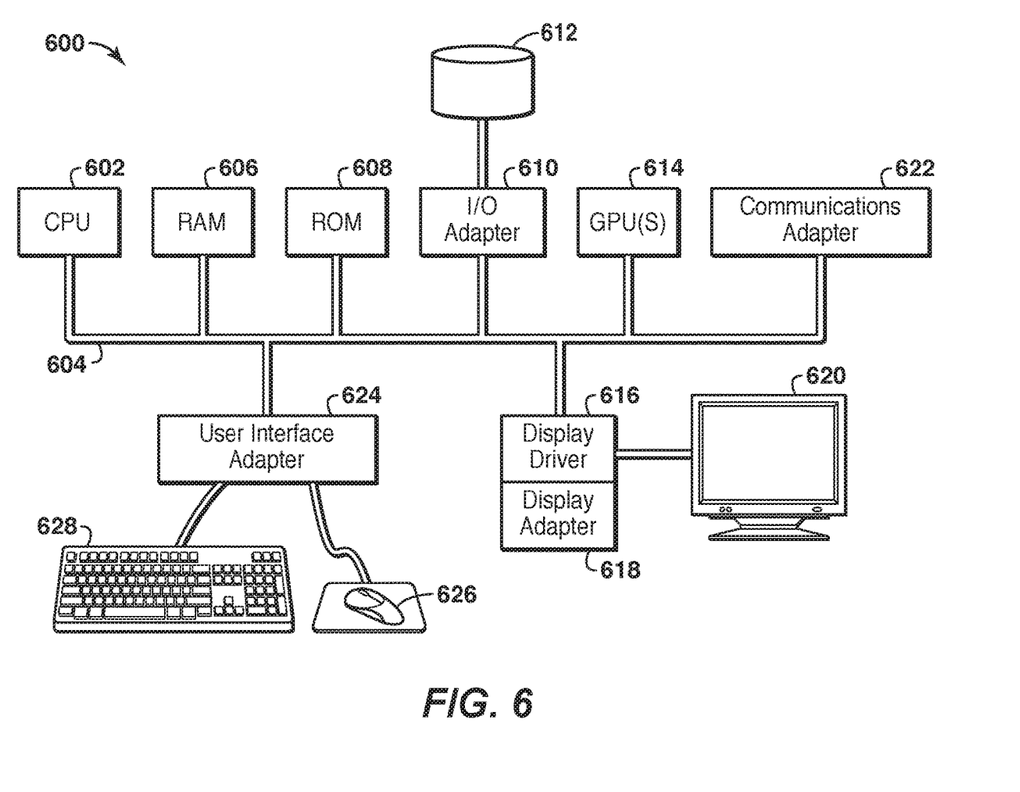
FIG. 6 is a block diagram of a computer system in accordance with an exemplary embodiment of the present techniques.

FIG. 6 is a block diagram of a computer system 600 in accordance with an exemplary embodiment of the present techniques. A central processing unit (CPU) 602 is coupled to system bus 604. The CPU 602 may be any general-purpose CPU, although other types of architectures of CPU 602 (or other components of exemplary system 600) may be used as long as CPU 602 (and other components of system 600) supports the inventive operations as described herein. The CPU 602 may execute the various logical instructions according to various exemplary embodiments. For example, the CPU 602 may execute machine-level instructions for performing processing according to the operational flow described above.

The computer system 600 may also include computer components such as a random access memory (RAM) 606, which may be SRAM, DRAM, SDRAM, or the like. The computer system 600 may also include read-only memory (ROM) 608, which may be PROM, EPROM, EEPROM, or the like. RAM 606 and ROM 608 hold user and system data and programs, as is known in the art. The computer system 600 may also include an input/output (I/O) adapter 610, GPU(s) 614, a communications adapter 622, a user interface adapter 624, and a display adapter 618. The I/O adapter 610, the user interface adapter 624, and/or communications adapter 622 may, in certain embodiments, enable a user to interact with computer system 600 in order to input information.

The I/O adapter 610 preferably connects a storage device (s) 612, such as one or more of hard drive, compact disc (CD) drive, floppy disk drive, tape drive, etc. to computer system 600. The storage device(s) may be used when RAM 606 is insufficient for the memory requirements associated with storing data for operations of embodiments of the present techniques. The data storage of the computer system 600 may be used for storing information and/or other data used or generated as disclosed herein. The communications adapter 622 may couple the computer system 600 to a network (not shown), which may enable information to be input to and/or output from system 600 via the network (for example, the Internet or other wide-area network, a local-area network, a public or private switched telephony network, a wireless network, any combination of the foregoing). User interface adapter 624 couples user input devices, such as a keyboard 628, a pointing device 626, and the like, to computer system 600. The display adapter 618 is driven by the CPU 602 to control, through a display driver 616, the display on a display device 620. Information and/or representations pertaining to a portion of a supply chain design or a shipping simulation, such as displaying data corresponding to a physical or financial property of interest, may thereby be displayed, according to certain exemplary embodiments.

The architecture of system 600 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

As an example, machine-readable logic or code may be used or executed with a computing system, such as computing system 600 of FIG. 6. The code or a set of instructions is provided enhancing hydrocarbon production, which may include analyzing hydrocarbon samples for geochemical signature comprising clumped isotope and/or position specific isotope geochemistry. When executed or applied with a computer system, such as computer system 600, code or set of instructions is configured to: analyze each of a plurality of hydrocarbon samples from the subsurface formation for a baseline geochemical signature, wherein the baseline geochemical signature is based on clumped isotope and/or position specific isotope geochemistry analysis; analyze sample data obtained from the subsurface location at a later time for a monitored geochemical signature, wherein the monitored geochemical signature is based on clumped isotope and/or position specific isotope geochemistry analysis; and compare the monitored geochemical signature with the baseline geochemical signature.

In addition, the set of instructions may be configured to provide other enhancements. For example, the set of instructions may be further configured to: adjust an exploration, development or production strategies based on the comparison; and display the adjusted an exploration, development or production strategies. Also, the set of instructions may be further configured to: convert each baseline geochemical signature into a baseline temperature and/or a baseline composition; and convert the monitored geochemical signatures into a monitored temperature and/or monitored temperature; and compare the monitored temperature with the baseline temperature and/or compare the monitored composition with the baseline composition. Further, the set of instructions may be further configured to: identify a source contribution for the monitored geochemical signature based on the baseline geochemical signature.

In addition, a monitoring module, which may be in fluid communication with a subsurface formation and the field deployable system, may be utilized as well. The monitoring module may include a set of instructions, wherein the set of instructions, when executed, are configured to: monitor produced fluids from the subsurface formation; and detect a specified event in the produced fluids. The set of instructions may be further configured to: detect of elevated hydrocarbon presence from a monitoring module; and transmit a notification to the field deployable system to analyze sample data obtained from the subsurface location at a later time for a monitored geochemical signature. The set of instructions may be further configured to: monitor for molecular changes in the produced fluids of one or more of methane, ethane, carbon dioxide, and nitrogen; monitor for bulk changes in mixtures of gases in the produced fluids; and/or monitor for stable isotope geochemistry changes in the produced fluid in one or more of carbon, hydrogen, nitrogen, and sulfur.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other.

What is claimed is:

1. A method for enhancing hydrocarbon production comprising:
   providing a field deployable system in fluid communication with a subsurface formation, wherein the field deployable system comprises mass spectrometric instrumentation that is in fluid communication with drilling equipment or attached to pipelines flowing produced fluids, and wherein the field deployable system is configured to measure a position specific isotope signature of a hydrocarbon compound, wherein the position specific isotope signature provides an indication of a concentration of at least one structurally distinct isotopologue of the hydrocarbon compound that contains at least one rare isotope;
   providing a mud sampling system in fluid communication with the subsurface formation;
   obtaining a plurality of mud gas samples from the mud sampling system and analyzing the mud gas samples to determine whether there the variation in signatures of the mud gas samples exceeds a predetermined threshold;
   when the variation in the signatures of the mud gas samples exceeds the predetermined threshold, obtaining one or more hydrocarbon samples from the subsurface formation at a first time and analyzing each of the hydrocarbon samples with the field deployable system to determine a baseline position specific isotope signature, wherein the hydrocarbon sample is a mud gas sample or a produced gas sample;
   when the variation in the signatures of the mud gas samples exceeds the predetermined threshold, obtaining one or more hydrocarbon sample from the subsurface formation at a second time, wherein the second time is after the first time, and analyzing each of the hydrocarbon samples with the field deployable system to determine a monitored position specific isotope signature, wherein the hydrocarbon sample is a mud gas sample or a produced gas sample;
   comparing the monitored position specific isotope signature with the baseline position specific isotope signature;
   hydraulic fracturing of a wellbore in the subsurface formation or adjusting an injection of gas or liquid into the subsurface formation based on the comparison; and
   producing hydrocarbons from the subsurface.

2. The method of claim 1, further comprising
   analyzing each of the hydrocarbon samples collected at the first time from the subsurface formation for a baseline geochemical signature and converting each baseline geochemical signature into a baseline temperature;
   analyzing each for the hydrocarbon samples collected at the second time from the subsurface formation for a monitored geochemical signature and converting the monitored geochemical signatures into a monitored temperature; and
   comparing the monitored temperature with the baseline temperature.

3. The method of claim 1, further comprising identifying a source contribution for the monitored position specific isotope signature based on the baseline position specific isotope signature.

4. The method of claim 1, wherein the second time is from 1 hour to 3 hours after the first time.

5. The method of claim 1 wherein the second time is based on a specified event.

6. The method of claim 5, wherein the specified event is the detection of elevated hydrocarbon presence from a monitoring module.

7. The method of claim 6, wherein the monitoring module comprises monitoring for changes in the mixture of hydrocarbon and non-hydrocarbon compounds in the sample.

8. The method of claim 7, wherein the monitoring module comprises monitoring for changes in the relative amounts of methane, ethane, carbon dioxide, and nitrogen in the sample.

9. The method of claim 6, wherein the monitoring module comprises monitoring for stable isotope geochemistry changes in one or more of carbon, hydrogen, nitrogen, and sulfur.

10. The method of claim 6, wherein the monitoring module comprises monitoring using mud gas and or produced gas sampling techniques to provide a quantitative analysis of certain hydrocarbon components.

11. The method of claim 6, wherein the monitoring module comprises monitoring changes in the produced gas.

12. The method of claim 6, wherein the specified event is a change in oil field operations.

* * * * *